US00PP21153P3

(12) United States Plant Patent

Alamo et al.

(10) Patent No.: US PP21,153 P3

(45) Date of Patent: Jul. 13, 2010

(54) BLUEBERRY PLANT NAMED 'CORONA'

(50) Latin Name: ***Vaccinium corymbosum* L.**
Varietal Denomination: Corona

(75) Inventors: Antonio Abad Alamo, Huelva (ES); José Ulf Hayler López, Huelva (ES); Paul M. Lyrene, Micanopy, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/289,178

(22) Filed: Oct. 22, 2008

(65) Prior Publication Data

US 2009/0210982 P1 Aug. 20, 2009

(30) Foreign Application Priority Data

Feb. 14, 2008 (QZ) ..... PBR 2008/0346

(51) Int. Cl.
*A01H 5/00* (2006.01)

(52) U.S. Cl. ..... Plt./157

(58) Field of Classification Search ..... Plt./157
See application file for complete search history.

*Primary Examiner*—June Hwu

(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers and forms fruit at mid-season. The attractive light blue flattened-round berries exhibit a classical blueberry flavor. The plant is very strong and grows well in various soil types. The plant commonly requires cross pollination, and displays a generally vase-shaped growth habit with attractive evergreen foliage. A low chilling requirement is also exhibited.

5 Drawing Sheets

Botanical/commercial classification: *Vaccinium corymbosum* L./Blueberry Plant.

Varietal denomination: cv. Corona.

SUMMARY OF THE INVENTION

The new Blueberry cultivar of the present invention was the product of controlled artificial pollination carried out in a greenhouse at Greenwood, Fla., U.S.A., wherein two parents were crossed during 1997 which previously had been studied in the hope that they would contribute the desired characteristics. The female parent (i.e., the seed parent) was the unreleased 'FL 95-54' cultivar (non-patented in the United States). The male parent (i.e., pollen parent) was the 'Jewel' cultivar (U.S. Plant Pat. 11,807). The parentage of the new cultivar can be summarized as follows:

'FL 95-54'×'Jewel'.

The seeds resulting from the pollination were shipped to Almonte, Huelva, Spain, where they sown during approximately 1998, small plants were obtained which were physically and biologically different from each other and selective research of the progeny was carried out. Selective study during the spring of 2002 resulted in the identification of a single plant of the new cultivar. This plant initially was designated S02-30-12.

It was found that the new Blueberry plant of the present invention displays the following combination of characteristics:

(a) flowers and forms fruit at mid-season, (b) displays a generally vase-shaped growth habit with attractive evergreen foliage that is well amenable for harvest, (c) commonly requires cross pollination for a good fruit set and quality, (d) displays a low chilling requirement, and (e) forms in abundance attractive large light blue flattened-round berries that exhibit a classical blueberry flavor.

The new cultivar well meets the needs of the horticultural industry and can be grown to advantage for the commercial production of blueberries. The plant is very strong and grows well in various soil types. The substantially round berries are well suited for machine harvest.

The new cultivar of the present invention can be distinguished from all Blueberry cultivars known to its originators. The 'FL 95-54' female parent plant is unreleased to the public and accordingly is not available to the public for use as a comparative cultivar. No comparative information is available concerning the distinguishing characteristics of the new cultivar when compared to the 'FL 95-54' parental cultivar. Also, since the 'FL 95-54' cultivar no longer exists, it is impossible to obtain such comparative information. When compared to the 'Jewel' parent plant, the new cultivar forms larger flowers, larger fruit, and larger leaves. When compared to the 'Misty' cultivar (non-patented in the United States), the 'Misty' cultivar forms considerably smaller berries of approximately 14 mm. When compared to the 'Windsor' cultivar (U.S. Plant Pat. No. 12,783), the 'Windsor' cultivar commonly displays a shorter growth habit that is more round in configuration. When compared to the 'O'Neal' cultivar (non-patented in the United States), the 'O'Neal' cultivar forms darker blue berries and reuires a longer chill requirement of approximately 500 hours. The new cultivar is less susceptible to Leaf Rust than the 'Blue Crisp' cultivar (U.S. Plant Pat. No. 11,033). When compared to the 'Star' cultivar (U.S. Plant Pat. No. 10,675), the 'Star' cultivar does not require cross-pollination for good fruit set and quality unlike the new cultivar. When compared to the 'Biloxi' cultivar (non-patented in the United States), the Biloxi cultivar is less resistant to Stem Blight.

The new cultivar has been asexually reproduced by the rooting of cuttings beginning during the summer of 2002 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Corona'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings, and were being grown outdoors at Almonte, Huelva, Spain.

DETAILED DESCRIPTION

Figure 1:
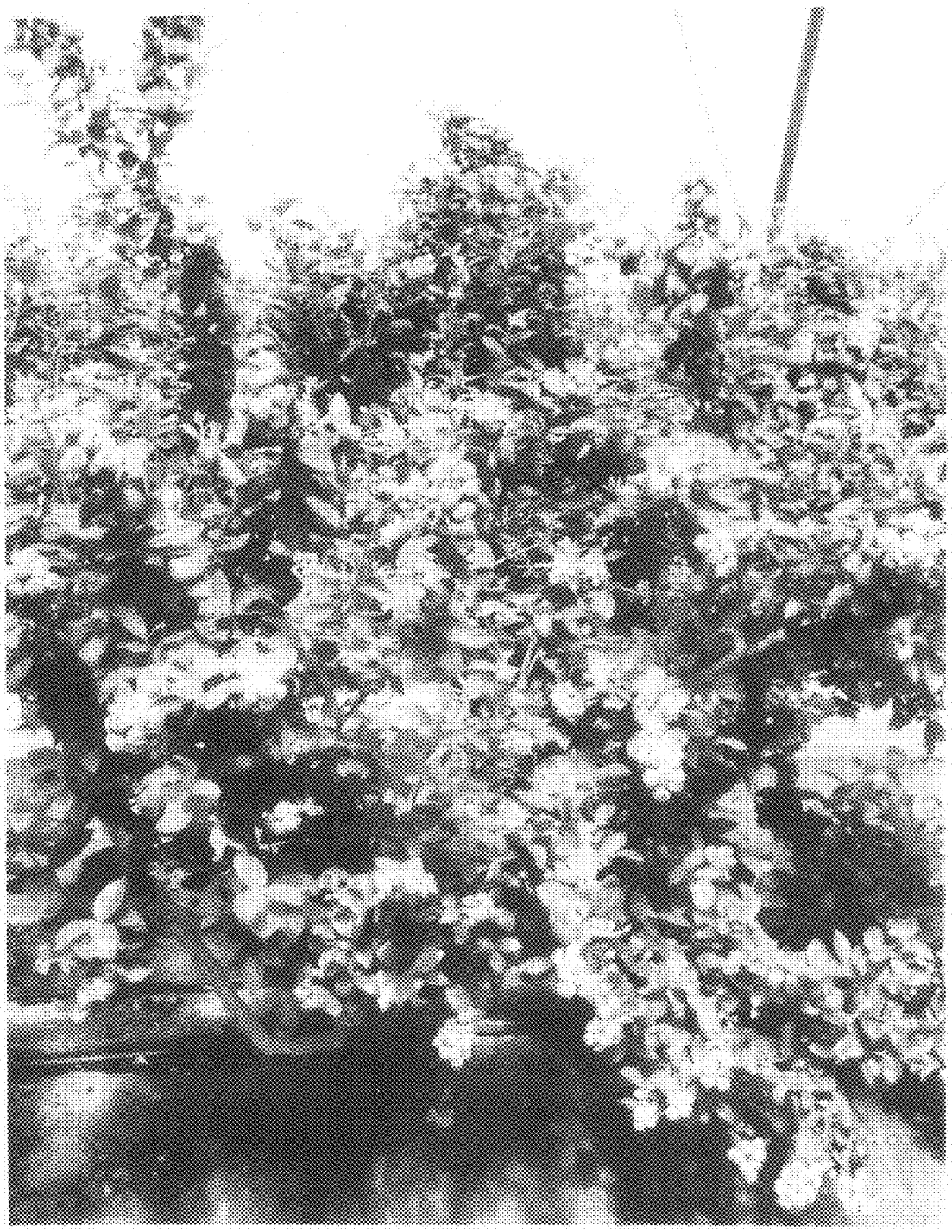
FIG. 1 shows an overall view of a typical fruiting plant of the new cultivar where the generally vase-shaped growth habit is illustrated.
Figure 2:
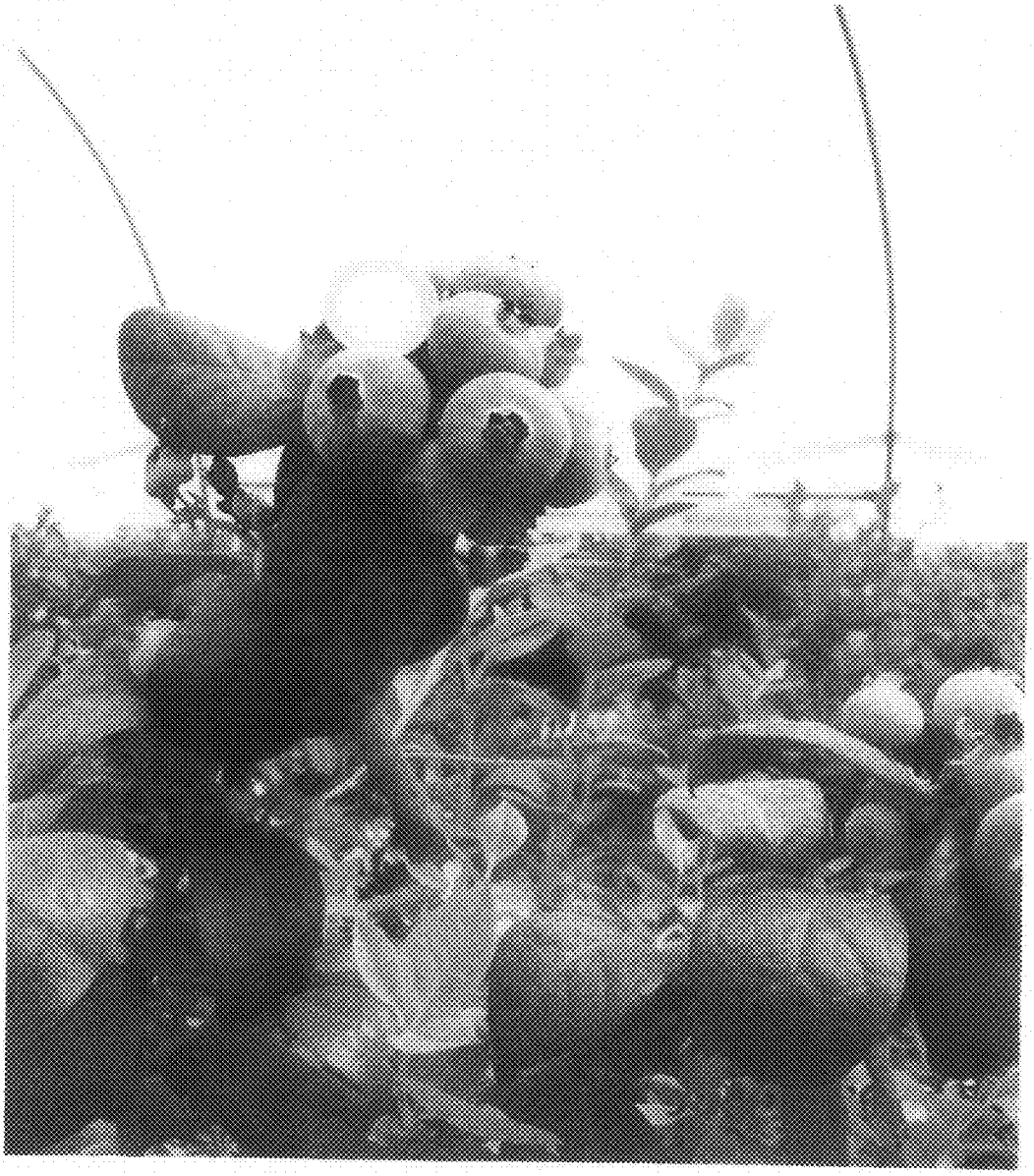
FIG. 2 shows typical berries of the new cultivar in various stages of maturity as well as the foliage. A one Euro coin is included for size comparison.
Figure 3:
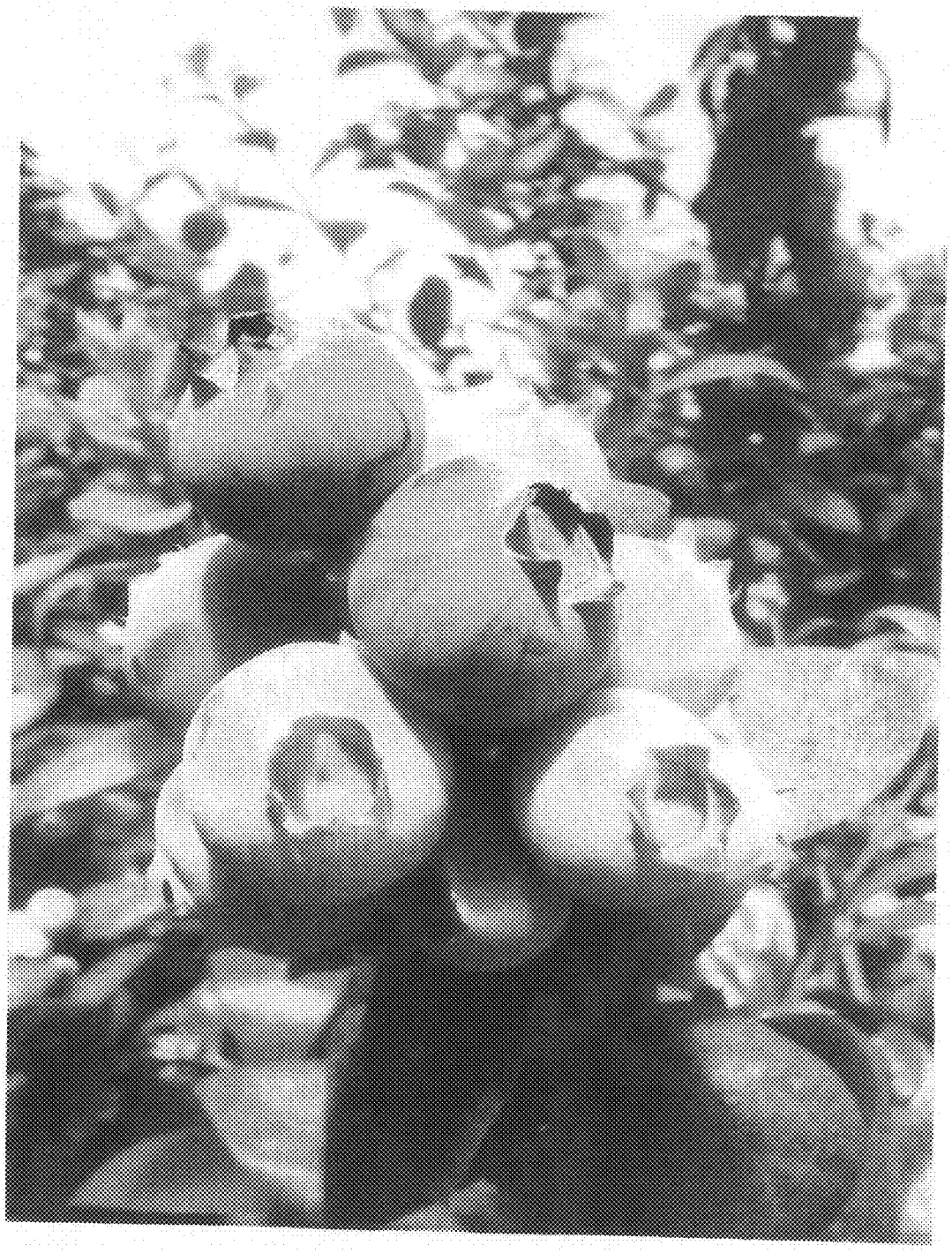
FIG. 3 shows a closer view of berries in various stages of maturity.
Figure 4:
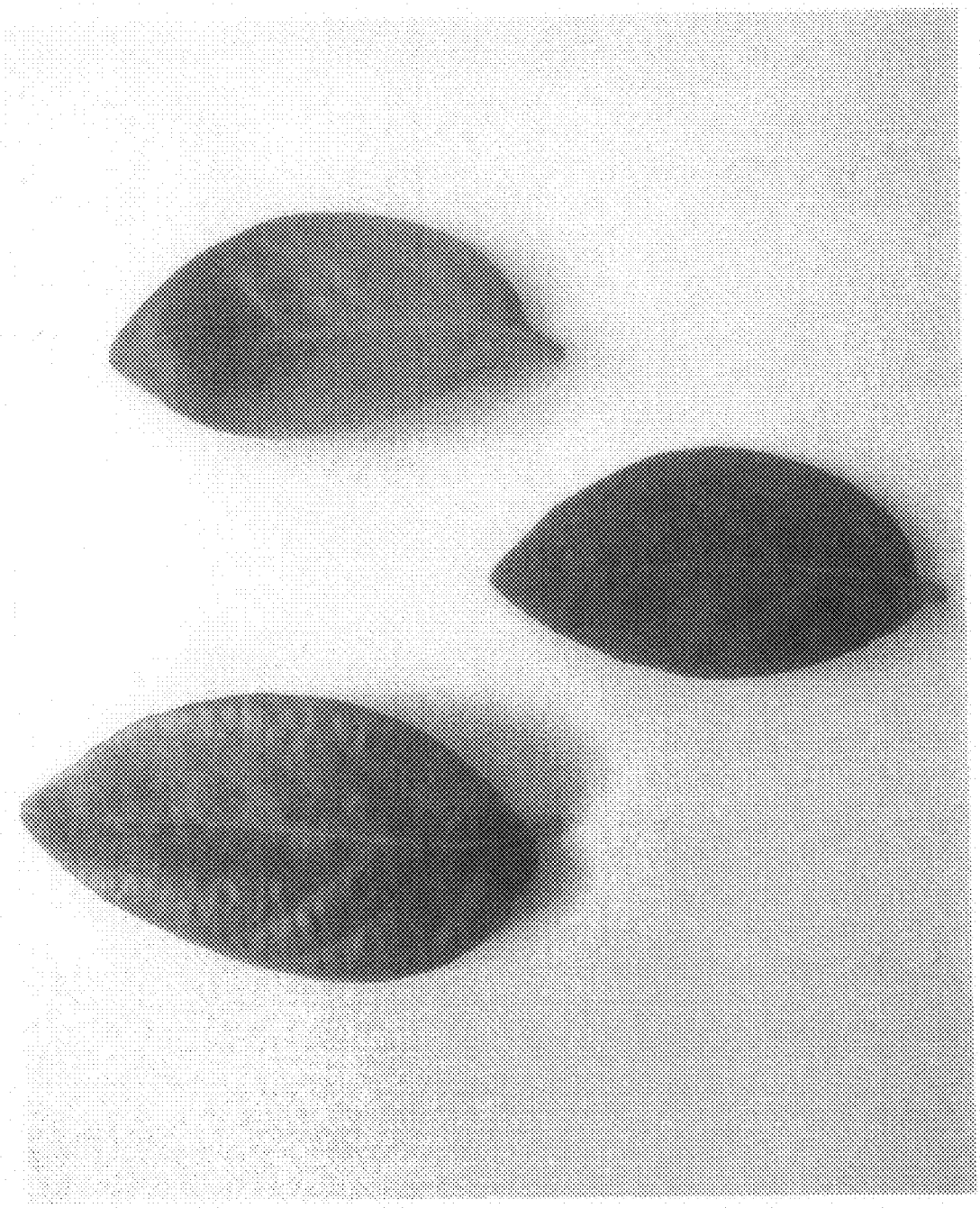
FIG. 4 shows upper (adaxial) surfaces of typical leaves of the new cultivar.
Figure 5:
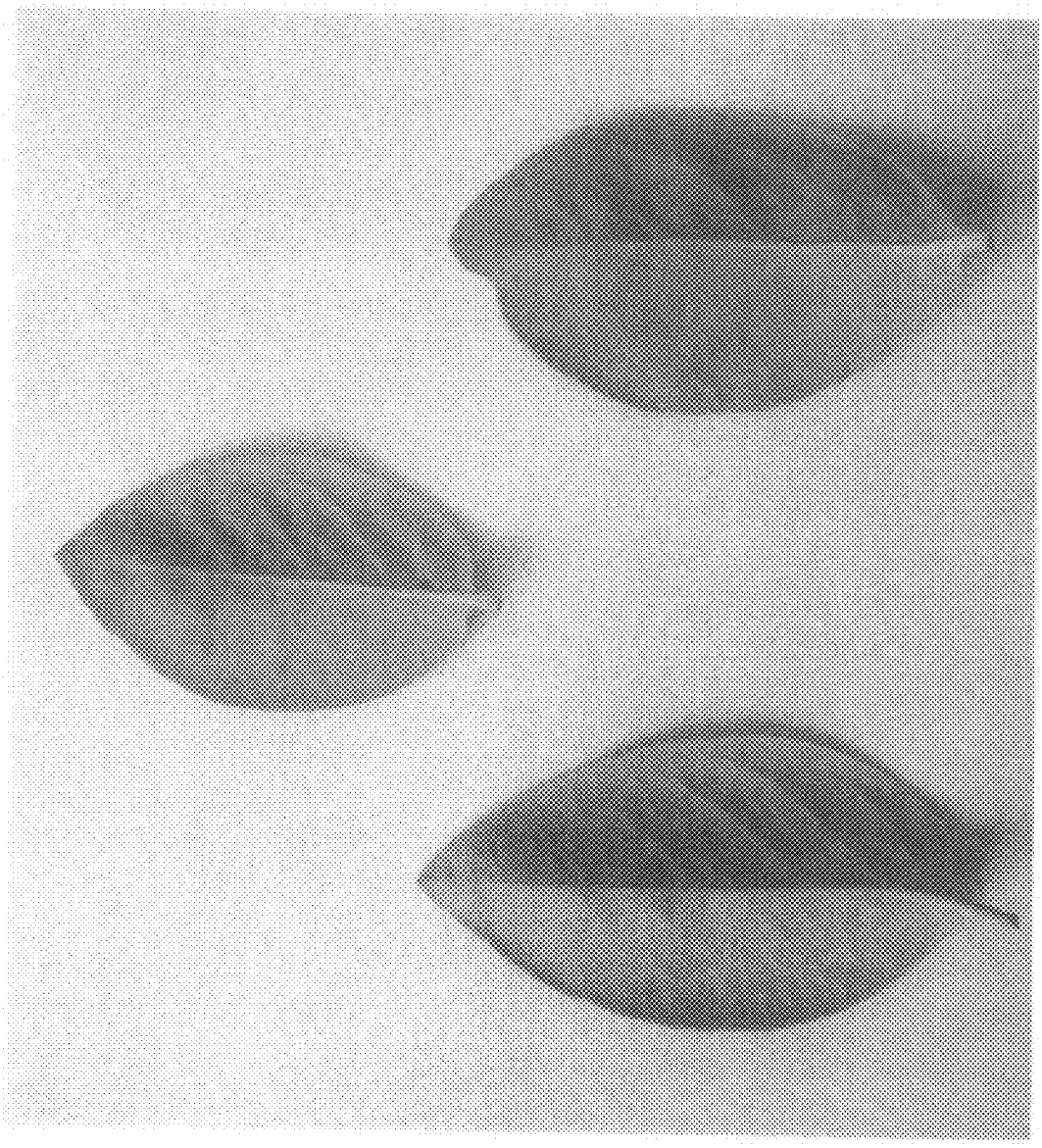
FIG. 5 shows under (abaxial) surfaces of typical leaves of the new cultivar.

The chart used in the identification of the colors described herein is The R.H.S. Colour Chart of The Royal Horticultural Society, London, England. Ordinary color terms are to be accorded their customary dictionary significance. The description is based on the observation of approximately five-year-old plants of the new cultivar which had been asexually reproduced by the rooting of softwood cuttings while growing outdoors at Almonte, Huelva, Spain.

Plant:

*Growth habit.*—Generally vase-shaped.

*Height.*—Approximately 1.8 m at 5 years of age.

*Width.*—Approximately 4.5 m at 5 years of age.

*Mature canes.*—Commonly approximately 46.6 cm in length on average, approximately 3.4 cm in diameter at the base on average, approximately 3 cm in diameter towards the tip on average, and near Grey-Brown Group 199D in coloration.

*Foliage retention.*—Evergreen.

*Chill requirement.*—Less than approximately 300 hours.

Foliage:

*Shape.*—Generally obtuse to elliptic (as illustrated).

*Length.*—Commonly approximately 67 mm on average.

*Width.*—Commonly approximately 40 mm on average.

*Apex.*—Acute.

*Base.*—Generally obtuse.

*Margin.*—Entire.

*Texture.*—Glabrous and non-glandular on both surfaces.

*Color.*—Green Group 137D on the upper (adaxial) surface, and Green Group 138B on the under (abaxial) surface.

*Petiole.*—Commonly approximately 3.9 mm in length on average, commonly approximately 1.8 mm in diameter on average, near Yellow-Green Group 145B in coloration on the upper surface, and near Yellow-Green Group 145C in coloration on the under surface.

Flowers:

*Time.*—Mid-season, at Almonte, Huelva, Spain, with first flower commonly at approximately January $7^{th}$, and 50 percent bloom at approximately February $10^{th}$.

*Number.*—Commonly approximately 7 flowers per inflorescence on average.

*Petals.*—5 in number and fused into a corolla tube.

*Corolla shape.*—Urceolate.

*Corolla size.*—The corolla tube commonly is approximately 8.8 mm in length on average, and approximately 10.3 mm in width on average at the widest point.

*Corolla color.*—Commonly near Green-White Group 157D.

*Sepals.*—Commonly 5 in number.

*Calyx.*—Commonly approximately 4.7 mm in length on average, a basin depth of approximately 1.4 mm, and a basin diameter of approximately 8.7 mm.

*Stamen.*—Commonly approximately 12 per flower.

*Filaments.*—Commonly non-adnate, pubescent, pale green in coloration and nearly transparent, and approximately 3.3 mm in length on average.

*Anthers.*—Bronze-colored, the pollen sac commonly is slightly darker in coloration than the pollen tube, and the size ratio of the pollen sac:pollen tube commonly is approximately 1:2.

*Pistil.*—One per flower and light green in coloration.

*Style.*—Commonly somewhat branched and flattened, commonly free at the base, approximately 10.2 mm in length on average, and commonly variable in thickness of approximately 0.3 to 1.8 mm.

*Peduncle.*—Commonly approximately 5.3 mm in length, approximately 1.2 mm in diameter, and the coloration is Yellow-Green Group 144D sometimes with coloration of Greyed-Red Group 179A on the upper surface.

*Fertility.*—Commonly not self-fertile. Representative pollinators include the 'Misty' cultivar (non-patented in the United States), 'Star' cultivar (U.S. Plant Pat. No. 10,675), 'Sharpblue' cultivar (non-patented in the United States), 'Romero' cultivar (U.S. Plant Pat. No. 20,373), 'Rocio' cultivar (U.S. Plant Pat. No. 20,374), 'Azulema' cultivar (U.S. Plant patent application Ser. No. 12/289,127, filed Oct. 21, 2008), and 'Altair' cultivar (U.S. Plant Pat. No. 20,830.

*Fragrance.*—none.

Fruit:

*Time.*—Commonly from approximately April 15th to June $7^{th}$ at Almonte, Huelva, Spain (i.e., approximately 8 weeks).

*Shape.*—Generally flattened-round.

*Height.*—Commonly approximately 19 mm on average.

*Width.*—Commonly approximately 21 mm on average.

*Weight.*—Approximately 4.76 g/berry on average when plants were 4 years of age.

*Fruit scar.*—Approximately 2.1 mm in size, and dry.

*Immature color.*—Commonly near Green Group 142B with bloom, and Yellow-Green Group 145B without bloom.

*Mature color.*—Light blue, Violet-Blue Group 97A with bloom, and Black Group 202A without bloom.

*Flesh color.*—Yellow-Green Group 154D.

*Productivity.*—Abundant, approximately 3.56 Kg/plant on average when plants were 4 years of age.

*Firmness.*—Medium.

*Flavor.*—Displays a pleasant acid blueberry flavor.

*Seed number.*—Somewhat variable, commonly approximately 10/berry, is influenced by level of pollination, commonly with more seeds being produced when pollination is greater.

*Seed shape.*—Broad kidney-shaped.

*Seed size.*—Commonly approximately 2 mm in length and approximately 1.1 mm in width.

*Seed color.*—Greyed-Orange Group 165B.

Development:

*Ability to store.*—The fruit stores well under refrigeration, when stored at 8° C. approximately 100 percent of the berries are of good quality 7 days after harvest, and when stored at 20° C. approximately 84 percent of the berries are of good quality 7 days after harvest.

*Disease tolerance.*—No special sensitivity to common Blueberry diseases. such as Leaf Rust (*Pucciniastrum vaccinii*) and *Botrytis* (*Botrytis cinerea*) has been encountered during observations to date at Almonte, Huelva, Spain. During observations to date the new cultivar is less susceptible to Leaf Rust than the 'Blue Crisp' cultivar, and is more resistant to Stem Blight than the 'Star' cultivar.

*Insects.*—Is susceptible to aphids and thrips.

*Cultural conditions.*—Is well suited for evergreen management under tunnels, and since the plant is very strong it is well adaptable to various types of soil.

*Heat resistance.*—Heat tolerant, has withstood temperatures as high as 45° C. at Almonte, Huelva, Spain.

*Cold resistance.*—Has withstood temperatures as low as −10° C. at Almonte, Huelva, Spain.

Plants of the 'Corona' cultivar have not been observed under all possible environmental conditions to date. Accordingly, it is possible that the phenotypic expression may vary somewhat with changes in light intensity and duration, cultural practices, and other environmental conditions without variance in the genotype.

We claim:

1. A new and distinct Blueberry plant that possesses the following combination of characteristics:

(a) flowers and forms fruit at mid-season, (b) displays a generally vase-shaped growth habit with attractive evergreen foliage that is well amenable for harvest, (c) commonly requires cross pollination for good fruit set and quality, (d) displays a low chilling requirement, and (e) forms in abundance attractive large light blue flattened-round berries that exhibit a classical blueberry flavor;

substantially as herein shown and described.

* * * * *